(12) United States Patent
Zhang

(10) Patent No.: US 9,814,723 B2
(45) Date of Patent: Nov. 14, 2017

(54) COMPOSITIONS AND METHODS FOR PROPHYLAXIS AND THERAPY FOR MENIERE'S DISEASE

(71) Applicant: Lixin Zhang, Williamsville, NY (US)

(72) Inventor: Lixin Zhang, Williamsville, NY (US)

( * ) Notice: Subject to any disclaimer, the term of this patent is extended or adjusted under 35 U.S.C. 154(b) by 49 days.

(21) Appl. No.: 14/730,740

(22) Filed: Jun. 4, 2015

(65) Prior Publication Data

US 2015/0265622 A1    Sep. 24, 2015

Related U.S. Application Data

(63) Continuation-in-part of application No. 14/183,148, filed on Feb. 18, 2014.

(60) Provisional application No. 61/768,414, filed on Feb. 23, 2013.

(51) Int. Cl.
*A61K 31/53* (2006.01)

(52) U.S. Cl.
CPC .................................. *A61K 31/53* (2013.01)

(58) Field of Classification Search
None
See application file for complete search history.

(56) References Cited

U.S. PATENT DOCUMENTS

| 8,273,900 B2 * | 9/2012 | Beattie | C07C 233/79 548/356.1 |
|---|---|---|---|
| 2002/0147196 A1 | 10/2002 | Quessy et al. | |

FOREIGN PATENT DOCUMENTS

WO    2006/121363 A1    11/2006

OTHER PUBLICATIONS

Kwan, P. et al., Lancet Neurol 2011; 10:88-90.*
Roberts, Catherine, "10 Signs and Symptoms of Meniere's Disease.", http://www.activebeat.co/your-health/10-signs-and-symptoms-of-menieres-disease/?utm_medium=cpc&utm_source=google&utm_campaign=AB_GGL_US_DESK&cus_widget=&utm_content=search_marketing&utm_term=menieres%20disease%20symptoms.*
Strupp et al., Therapeutic Advances in Neurological Disorders, 2009 2(4), 223-239. Jan. 1, 2009.
Juhn et al., Effect of Stress-related hormones on inner ear fluid homeostasis and function, Am. J. Otol. Nov. 20, 1999 (6) 800-6. Nov. 20, 1999.
Bikhazi, P., et al., Efficacy of antimigrainous therapy in the treatment of migraine-associated dizziness, American Journal of Otolaryncology, 1997, vol. 18, No. 3, pp. 350-354.
Radtke, A., et al., Migraine and Meniere's disease: is there a link?, Neurology, 2002, vol. 59, pp. 1700-1704.
Sajjadi, H., et al., Meniere's disease, Lancet, 2008, vol. 372, pp. 406-414.
Strupp, M., et al., Pharmacotherapy of vestibular and ocularmotor disorders including nystagmus, Neurology, 2011, vol. 258, pp. 1207-1222.
McCall, A.A., et al., Drug delivery for treatment of inner ear disease: current state of knowledge, Ear & Hearing, 2010, vol. 31, No. 2, pp. 156-165.
Strupp et al., Pharmacological advances in the treatment of neuro-otological and eye movement disorders, Current Opinion in Neurology, 2006, vol. 19, pp. 33-40.
Lempert, T., et al., Epidemiology of vertigo, migraine and vestibular migraine, Journal of Neurology, 2009, vol. 256, No. 3, pp. 333-338.
Neuhauser, H., et al., The interrelations of migraine, vertigo, and migrainous vertigo, Neurology, 2001, vol. 56, pp. 436-441.
Staab, J. et al., A prospective trial of sertraline for chronic subjective dizziness, The Laryngoscope, 2004, vol. 114, pp. 1637-1641.
Horii, A., et al., Effects of fluvoxamine on anxiety, depression, and subjective handicaps of chronic dizziness patients with or without neuro-otologic diseases, Journal of Vestibular Research, 2007, vol. 17, pp. 1-8.
Berlinger, N.T., Miniere's Disease: New concepts, new treatments, Minnesota Medicine, Nov. 2011; www.minnesotamedicine.com/PastIssues/PastIssues2011/November2011/MenieresDisease.aspx.

* cited by examiner

*Primary Examiner* — Sreeni Padmanabhan
*Assistant Examiner* — Jeanmarie Calvillo
(74) *Attorney, Agent, or Firm* — Hodgson Russ LLP

(57) ABSTRACT

Provided are articles of manufacture, compositions and methods for prophylaxis and/or therapy for disorders involving dizziness and/or vertigo. The articles of manufacture and compositions contain lamotrigen and/or bupropion. The compositions include pharmaceutical compositions which are intended to alleviate dizziness and/or vertigo. In certain aspects the disclosure includes articles of manufacture and kits which include printed material which provides an indication that the articles or compositions are intended to be used for prophylaxis and/or therapy of Meniere's Disease or a symptom thereof.

3 Claims, 7 Drawing Sheets

COMPOSITIONS AND METHODS FOR PROPHYLAXIS AND THERAPY FOR MENIERE'S DISEASE

CROSS REFERENCE TO RELATED APPLICATIONS

This application is a continuation-in-part of U.S. application Ser. No. 14/183,148, filed Feb. 18, 2014, now pending, which claims priority to U.S. application No. 61/768,414, filed Feb. 23, 2013, the disclosures of each of which are incorporated herein by reference.

FIELD OF THE INVENTION

The present invention relates generally to compositions and methods for prophylaxis and therapy of several types of dizziness.

BACKGROUND OF THE INVENTION

Dizziness and imbalance problems affect more than 90 million Americans and are one of the most common complaints in clinic patients. These symptoms can be caused by a range of vestibular and neurological disorders, but almost two-thirds of dizziness cases are a result of Meniere's disease, migraine-associated vertigo (MAV), and phobic postural vertigo/chronic subjective dizziness (PPV/CSD). The etiology of all these disorders is still unclear and successful pharmaceutical treatments are lacking Meniere's Disease In 1861 Prosper Meniere first published an article describing an inner ear disorder that caused vertigo and hearing loss.[i] Today the disorder, known as Meniere's disease (MD) affects 20 to 200 per 100,000 individuals with men and women (typically between 30-50 years old) being affected almost equally.[ii] Meniere's disease continues to be characterized by the same symptoms described in 1861. The American Academy of Otolaryngology—Head and Neck Surgery (AAO-HNS) criteria for diagnosis includes recurrent spontaneous and episodic vertigo (vertigo that is debilitating and usually causes nausea or vomiting without loss of consciousness) that lasts at least 20 minutes and up to several days with hearing loss, aural fullness and/or tinnitus.[iii] This vestibular disorder has several proposed causes, but is truly idiopathic due to inconsistent symptoms without explanations. It is commonly thought that endolymphatic hydrops causes Meniere's disease.[iv] Hydrops form either because a blockage prevents the endolymphatic fluid from being properly absorbed or because there is an excess in endolymphatic fluid production. The resulting increase in inner ear pressure is proposed to then cause vertigo attacks and the aural fullness sensation characteristic of Meniere's disease.[v] However, hydrops may be an epiphenomenon rather than the primary cause because it is not found in every Meniere's patient. Additionally, one study has discovered that animal models do not present differences in hydrostatic pressures in the perilymph and endolymph despite the presence of significant hydrops.[vi] Other underlying causes of Meniere's disease have been researched, like spreading depression and characteristically similar migraines.

Migraine has been frequently associated with Meniere's disease and the two disorders share several likenesses. A study on the comorbidity of migraine and Meniere's disease found a significantly higher lifetime prevalence of migraine in the MD group compared to an age- and sex-matched control group: 44 out of 78 patients with MD (56%) had a history of migraine compared to 20 out of 78 in the control group (25%) for both men and women.[vii] The same study found that 35 (45%) patients reported Meniere's attacks were always accompanied by at least one migrainous symptom (migrainous headaches, photophobia, or aural symptoms) and 9 (11%) patients reported Meniere attacks were sometimes accompanied by migrainous symptoms. In our own research on dizziness and balance disorders between 2011 and 2012 we found that 90 patients were diagnosed with Meniere's disease and of these patients 13 (14%) individuals were diagnosed with migraine and 10 (11%) individuals were diagnosed with anxiety and migraine, composing a total of 23 (25%) patients who were diagnosed with some form of migraine. Both vestibular disorders have a similar non-drug treatment as well, including avoidance of caffeine, chocolate, alcohol, tobacco and salt.[viii] Additionally, Meniere's disease and migraines both have significant genetic components and it is possible that patients are inheriting ion channel abnormalities shared by the brain and inner ear that causes both disorders.[ix] It has not been definitively determined whether migraine mimics Meniere's disease or causes it, but the several commonalties suggest that MD patients with migraine may find relief with anti-migrainous medication.

Anxiety is another diagnosis frequently seen with Meniere's disease (MD). Many MD patients become anxious, depressed or stressed due to the severe repeated vertigo. This anxiety can even develop into a secondary vestibular disorder: phobic postural vertigo (or chronic subjective dizziness if symptoms persist for more than 3 months). A study assessed MD patients using the Dutch Daily Hassles List, Coping Inventory for Stressful Situations (CISS), Symptoms Checklist 90 (SCL-90), NEO Five Factor Inventory (NEO-FFI), General Health Questionnaire (GHQ-12), and the Short Form Health Survey 36 (SF-36).[x] The results showed that Meniere's disease patients did not have any abnormalities in personality, but had more daily stressors, had a worse quality of life and more instances of anxiety and depression compared to a healthy control group. These psychological difficulties were more profound in patients who had been living with Meniere's disease for a longer time and in those who experienced more frequent symptoms. Another study found that more than half of the 800 Meniere's patients enrolled reported experiencing partial or full posttraumatic stress disorder symptoms.[xi] Our own preliminary analysis revealed a similar pattern of anxiety comorbidities with, again 10 (11%) of 90 MD patients diagnosed with both anxiety and migraine and 26 (29%) patients diagnosed with only anxiety. These numbers combined with migraine prevalence totaled to slightly more than half (54%) of our total MD sample with an anxiety and/or migraine comorbidity. However, most treatments for Meniere's disease do not address migraine or anxiety symptoms.

In addition to the aforementioned lifestyle and diet changes, Meniere's disease can be treated in a variety of ways, all of which are short of being complete successes for one reason or another. Streptomycin therapy, while effective in vertigo control, after repeated treatments has an ototoxic effect and must be stopped if the patient experiences a rapid decline in vestibular function, develops hearing loss or manifests oscillopsia.[xii] Intratympanic gentamicin also has a high rate of sensorineural hearing loss.[xiii] The efficacy of invasive surgery is questionable as well. A study conducting both endolymphatic sac surgeries and mastoidectomies indicated that the benefits of endolymphatic sac surgery may be a surgical placebo effect.[xiv] Patients who undergo vestibular neurectomies rarely have a reoccurrence of vertigo and have no risk of hearing loss. Despite these positive results, the procedure is very stressful and older patients are ineligible because of the greater difficulty to compensate for lost vestibular function. Irrefutably the treatment with the least side effects is the Meniett device, but many patients cannot afford the device priced around $3,500 because of reluctant insurers. A lot of pharmacotherapy research has been conducted too; however, few have advanced to clinical usage. Most studies, such as those on the effects of betahistine, do not meet high methodological standards and the evidence is deemed inconclusive.[xv] Most importantly, the majority of these treatments are merely symptomatic and an effective prophylactic intervention has not yet been developed.

Migraine-Associated Vertigo (MAV)

Beyond the many commonalties shared between migraines and Meniere's disease, migraines also have their own frequent comorbidity with vertigo and dizziness. In a study conducted by Kayan and Hood, motion sickness was reported by over half of the participants diagnosed with migraine.[xvi] Another study revealed 3.2% comorbidity between migraine and vertigo in the general population despite an expected overlap of only 1.1% by chance alone.[xvii] Researchers reasoned that this increased prevalence could be due to a higher occurrence of dizziness and vertigo symptoms in migraine patients than in controls, but also could be caused by the recent recognition of migraine-associated vertigo (MAV) as its own vestibular disorder. The details of migraine-associated vertigo regarding terminology, causation, criteria, and treatment are still highly debated. However, Neuhauser et al.'s criteria have been commonly used to diagnosis patients.[xviii] Definite migraine-associated vertigo is based on the patient having episodic vestibular symptoms of at least moderate severity (rotational vertigo, other illusory self or object motion, positional vertigo or head motion intolerance), migraine according to the International Headache Society (IHS) criteria, at least one migrainous symptom during at least two vertiginous attacks (migrainous headache, photophobia, phonophobia, or visual or other auras), and all other causes ruled out by appropriate investigations. A probable diagnosis of migraine-associated vertigo is based on episodic vestibular symptoms of at least moderate severity; at least one migraine according to the IHS criteria, migrainous symptoms during vertigo, migraine-specific precipitants of vertigo (specific foods, sleep irregularities, hormonal changes), or response to anti-migraine drugs; and all other causes ruled out by appropriate investigations. There are more women than men with symptoms of migraine; in the United States rates range from 16-18% for women and 5-6% for men.[xix] Although general population prevalence rates have not been calculated, if sample study statistics are reflective of the population it would be expected that 4.5% of women and 1.5% of men in the U.S. experience migraine associated vertigo. Yet, because the exact mechanisms of this disorder are still debated, effective prophylactic treatment that could greatly improve the quality of life for these individuals has not been implemented.

Most MAV patients are given medications that will only abort symptomatic vertigo and migraine attacks once they are already occurring. These medications include benzodiazepines (Valium), cyproheptadine, ergots, methysergide, non-steroidal anti-inflammatory drugs (Ibuprofen), opiates or triptans (Maxalt, Relpax).[xx] Nonpharmacologic remedies include butterbur root extract, dietary restrictions (caffeine), food supplements, magnesium, and better sleep hygiene. Common prophylactic treatments for migraine such as beta-blockers, calcium antagonists, anticonvulsants (topiramate or depakote) and antidepressants are frequently being used in MAV cases, although it is still debated whether these medications have a positive effect on both migraine and vertigo aspects of MAV. All of these treatment options lack a high-level of evidence and randomized controlled study designs. Further complicating efficient treatment for MAV patients is anxiety comorbidity and anxiety-related dizziness (PPV). It is well recognized that migraine commonly occurs with symptoms of depression and anxiety. For instance, the life time prevalence of panic disorder is 16% in patients with migraine compared with 4% in control groups.[xxi] Eckhardt-Henn et al. concluded that migraine-associated vertigo and Meniere's disease seem to be the vestibular disorders with the highest risk of secondary anxiety symptoms.[xxii] An approach that embraces both prophylactic MAV treatment and anti-anxiety medication will provide patients with the most relief, but such an approach has not previously been available. The present invention meets these and other needs related to prophylaxis and therapy of dizziness with several distinct etiologies.

SUMMARY

The present disclosure relates to compositions and methods for prophylaxis and/or therapy of dizziness in an individual. In embodiments, the disclosure provides a pharmaceutical formulation comprising lamotrigine and/or bupropion hydrochloride in a therapeutically effective amount for prophylaxis and/or therapy of dizziness in an individual. In embodiments, the compositions comprise only lamotrigine. Methods are provided for use in prophylaxis and/or therapy of one or more symptoms of Meniere's Disease. In embodiments, the disclosure encompasses administering to an individual an individual diagnosed with Meniere's Disease a composition comprising lamotrigine such that dizziness associated with the Meniere's Disease is reduced, or is eliminated. In embodiments, lamotrigine is the only bioactive compound in the composition. In embodiments, lamotrigine is the only sodium channel blocking drug in the composition. In embodiments, the composition used to treat the individual does not comprise a diuretic agent. In embodiments, the composition used to treat the individual does not comprise any of diazepam, lorazepam, promethazine, dimenhydrinate or meclizine hydrochloride. Thus, the disclosure includes administering a composition comprising lamotrigine to an individual with Meniere's Disease such that dizziness is reduced or eliminated, and wherein the lamotrigine is the only drug the individual is taking that results in the effect on dizziness is lamotrigine.

In one embodiment, the disclosure includes a pharmaceutical composition comprising lamotrigine packaged in a packaging material which comprises printed material on or in the packaging. The printed material includes an indication that the composition is for use in the treatment of dizziness and/or vertigo. In an embodiment, the disclosure includes a pharmaceutical composition comprising lamotrigine packaged in a packaging material and identified in print in or on the packaging material that the composition is for use in the treatment of Meniere's Disease. In embodiments, the packaging material includes information related to a prescription for use of the pharmaceutical composition in the prophylaxis and/or therapy of Meniere's Disease, and may include such information as dosage route, frequency and duration of administration.

In another aspect the disclosure include a kit comprising a therapeutically effective amount of lamotrigine, packaged in a container, the kit further comprising a label attached to or packaged with the container, the label describing the contents of the container and providing indications and/or instructions regarding use of the contents of the container to treat dizziness and/or vertigo and/or Meniere's Disease.

In another aspect the disclosure includes an article of manufacture comprising packaging material and lamotrigine provided in a separate or in a single pharmaceutical formulation in the packaging material, wherein the pharmaceutical composition is effective for the treatment of a subject in need of prophylaxis or therapy for anti-dizziness/vertigo, and wherein the packaging material optionally comprises a label which indicates that the lamotrigine can be used for at least ameliorating the symptoms of Meniere's Disease and/or dizziness and/or vertigo.

DETAILED DESCRIPTION OF THE INVENTION

Figure 1:
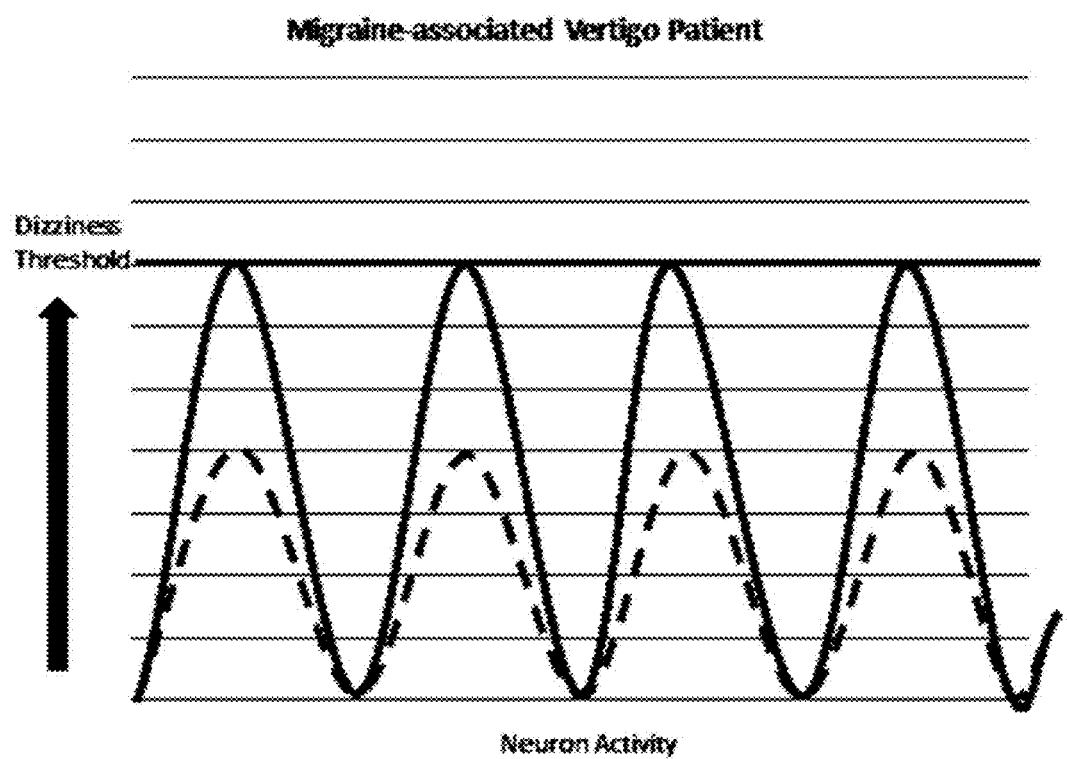
FIG. 1: The graph indicates normal neuronal activity and presumed normal dizziness threshold. The solid wave line suggests the increased neuronal activity in patients with migraine-associated vertigo.
Figure 2:
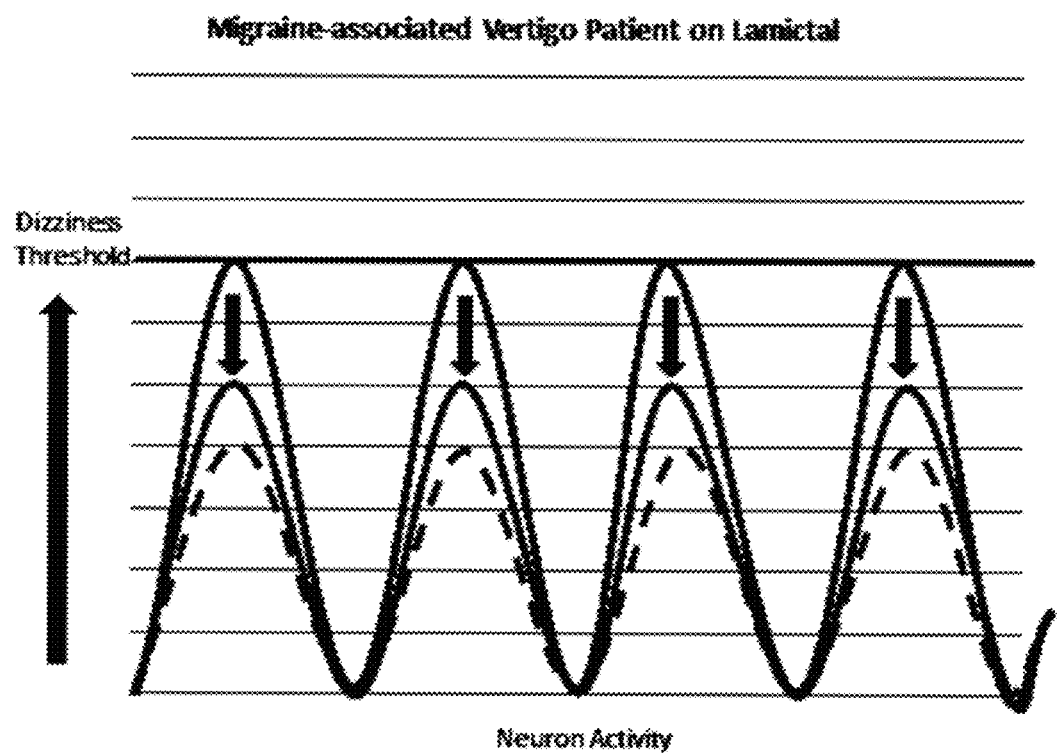
FIG. 2: We propose that Lamotrigine may be able to suppress the neuronal hyperactivity and prevent the dizziness threshold from being reached, thus preventing dizziness and migraine.
Figure 3:
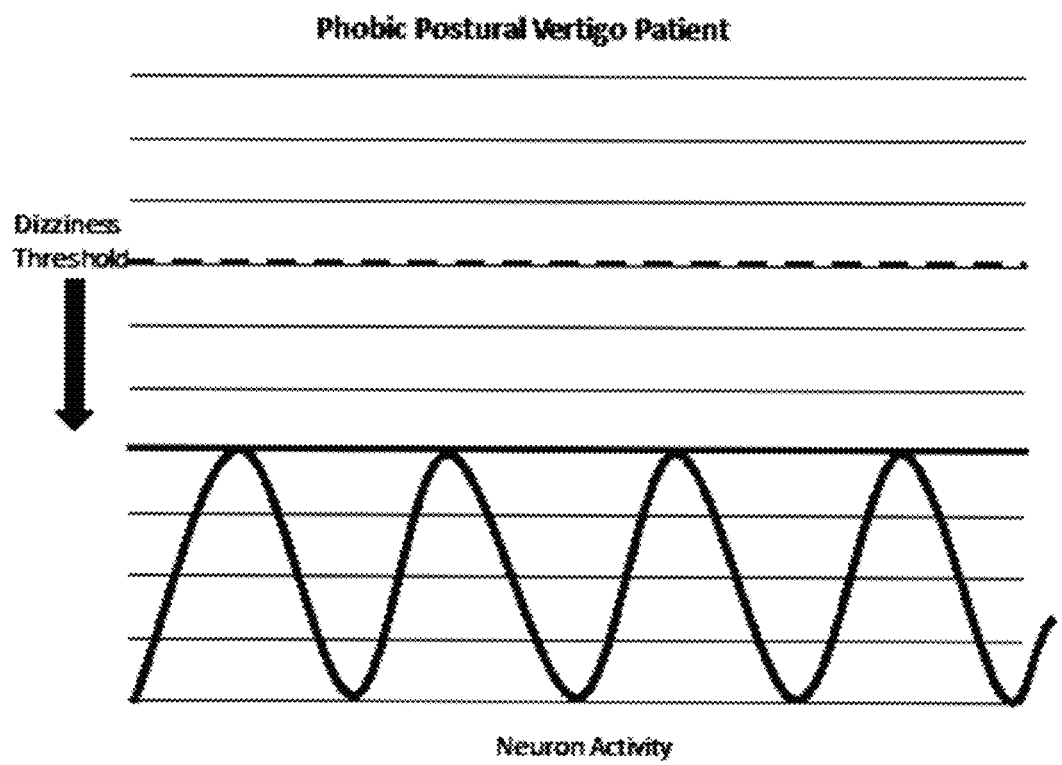
FIG. 3: Patients with phobic postural vertigo may have pre-existing low dizziness thresholds, which explains why patients are very sensitive to motion, light, noise, stress, and, in severe situations, may experience dizziness constantly.
Figure 4:
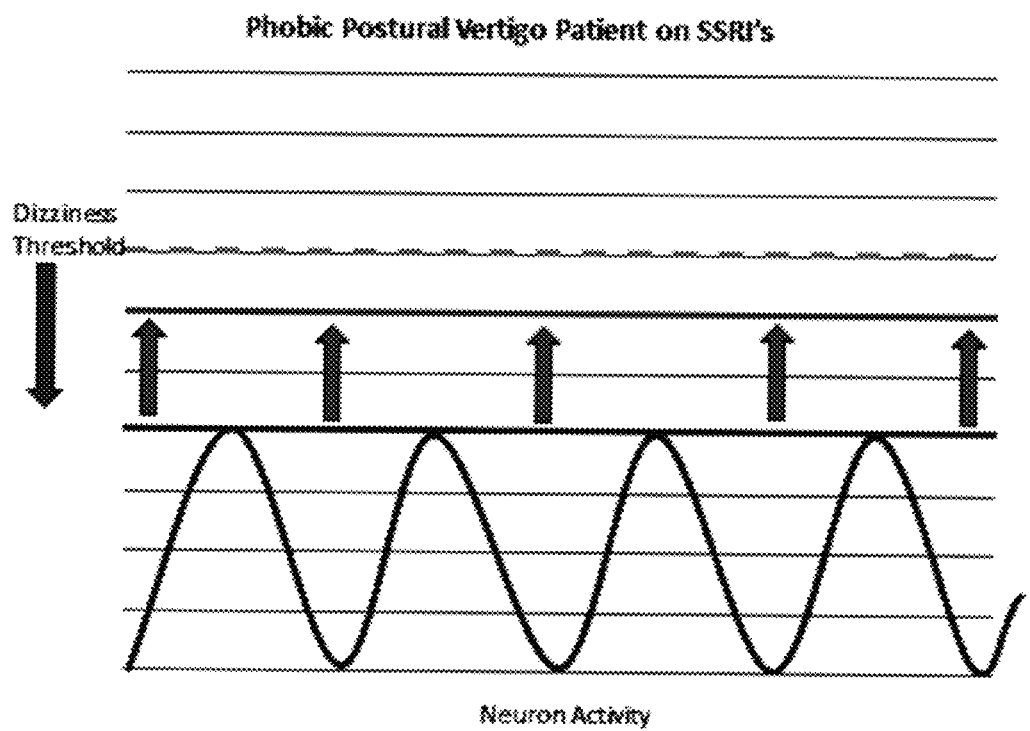
FIG. 4: Anti-anxiety medications may be able to raise the dizziness threshold and treat the PPV dizziness.
Figure 5:
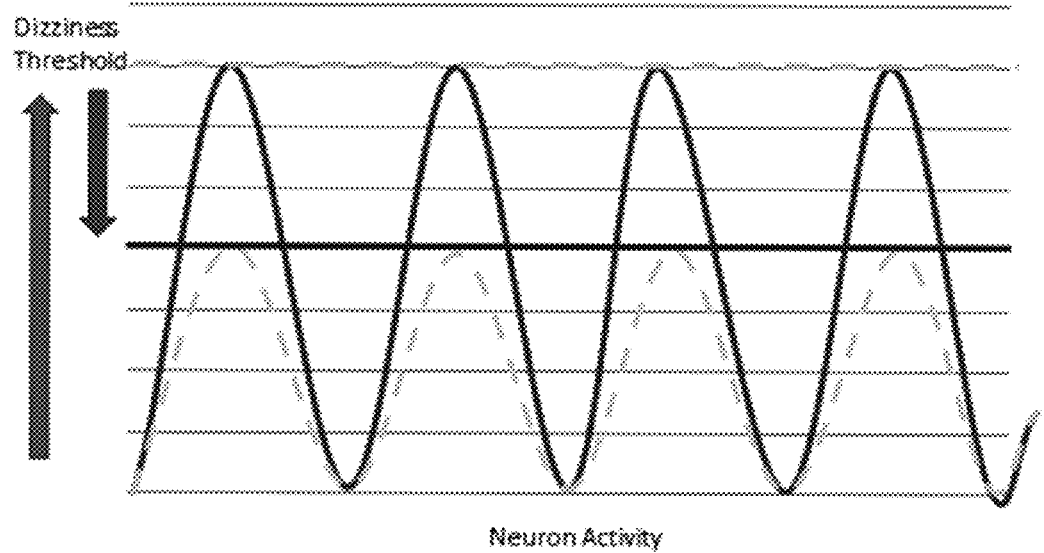
FIG. 5: The graph demonstrates how dizziness patients can have both a low dizziness threshold and neuronal hyperactivity with a co-existing MAV and PPV diagnosis.
Figure 6:
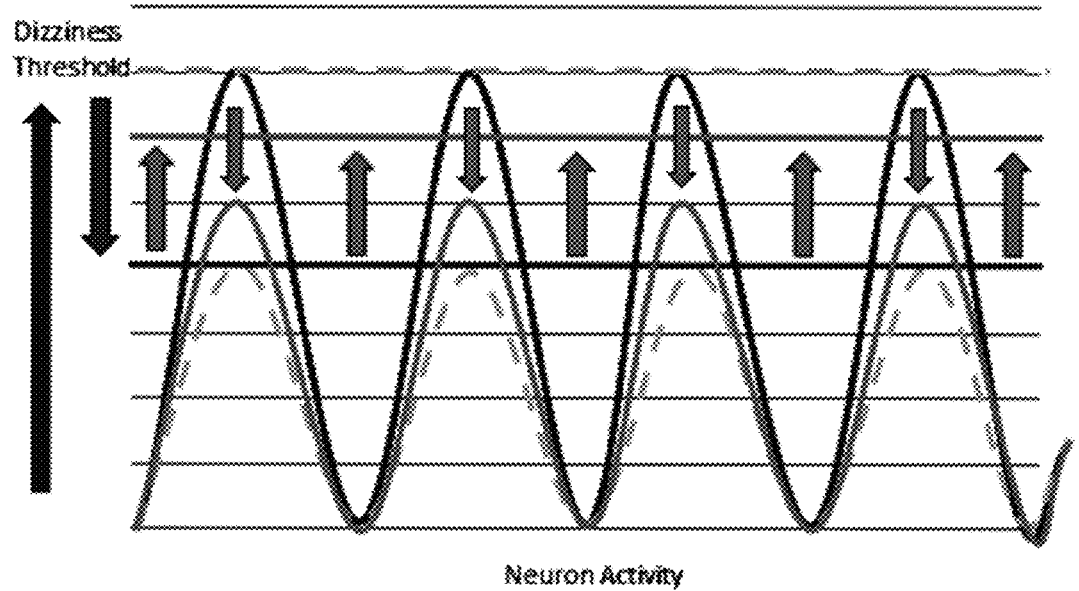
FIG. 6: The combination of Lamictal and WELLBUTRIN can suppress the neuronal hyperactivity and raise the dizziness threshold, which without intending to be constrained by theory, we believe achieved the optimal effectiveness.

The present disclosure provides compositions and methods for prophylaxis and/or therapy of vertigo and/or dizziness. The vertigo and/or dizziness for which a prophylactic and/or therapeutic benefit is provided can be vertigo and/or dizziness in the absence of any associated neurological disorder, or it can be associated with any of several disorders, or combinations of such disorders, including but not necessarily limited to Meniere's Disease and Migraine-associated Vertigo (MAV).

In one aspect, the invention includes a method for prophylaxis and/or therapy of Meniere's Disease. In general, the method comprises administering to an individual diagnosed with or suspected of having Meniere's Disease a composition of the invention in an amount effective to prevent or lessen the severity of dizziness, or to reduce the number of attacks, such as vertigo attacks, during a treatment period.

The terms "vertigo" and "dizziness" as used herein have art recognized meanings and can be readily diagnosed by the skilled artisan and include imbalance and/or the sensation of the individual or the individual's environment spinning, moving to a non-horizontal plane, or that the individual is about to fall. Likewise, diagnosis of Meniere's Disease and its symptoms, including but not necessarily limited to dizziness associated with it, can readily be performed by those skilled in the art.

In one embodiment, the disclosure includes a closed or sealed package that contains lamotrigine alone, or lamotrigine and bupropion in the same or as separate pharmaceutical compositions. In embodiments, only lamotrigine is included as an active drug in a closed or sealed package that has one or more closed or sealed vials, bottles, blister (bubble) packs, or any other suitable packaging for the sale, or distribution, or use of pharmaceutical agents. In addition to the pharmaceutical compositions, the package may contain printed information. The printed information can be provided on a label, or on a paper insert, or printed on the packaging material itself. The printed information can include information that identifies the lamotrigine, the amounts and types of active and inactive ingredients, an indication of what condition the pharmaceutical composition(s) is intended to treat, and instructions for taking the pharmaceutical composition, such as the number of doses to take over a given period of time, and whether or not it should be taken with certain types of foods or liquids. In one embodiment, the packaging and/or the pharmaceutical agents themselves is marked with the term LiveWell, or a variation of that term. Thus, in various embodiments the invention includes: i) a pharmaceutical composition of the invention packaged in a packaging material and identified in print, or in or on the packaging material, that the composition is for use in the treatment of Meniere's Disease, or another disease or disorder that is has as a symptom dizziness/vertigo; ii) a kit comprising a therapeutically effective amount of a composition of the invention, packaged in a container, the kit further comprising a label attached to or packaged with the container, the label describing the contents of the container and providing indications and/or instructions regarding use of the contents of the container to treat Meniere's Disease, or another disease or disorder that is has as a symptom dizziness/vertigo; iii) a pharmaceutical product comprising pharmaceutical packaging; and a solid formulation inside the packaging, wherein the formulation comprises lamotrigine, the product further comprising printed material with instructions for using the product to treat Meniere's Disease, or another disease or disorder that is has as a symptom dizziness/vertigo; iv) an article of manufacture comprising packaging material and at least one pharmaceutical composition as described herein contained within the packaging material, wherein the pharmaceutical composition is effective for the treatment of a subject in need of anti-dizziness/vertigo prophylaxis or therapy, and wherein the packaging material optionally comprises a label which indicates that the pharmaceutical composition can be used for at least ameliorating the symptoms of Meniere's Disease, or another disease or disorder that is has as a symptom dizziness/vertigo. In certain embodiments, the printed information that is part of the product and/or packaging relates to prophylaxis or therapy of a condition that has as a symptom dizziness/vertigo, wherein that condition is MAV or PPV.

Lamotrigine

Lamotrigine is marketed in the U.S. and Europe under the trade name LAMICTAL. Lamotrigine has the chemical formula 6-(2,3-Dichlorophenyl)-1,2,4-triazine-3,5-diamine. It has the molecular formula $C_9H_7Cl_2N_5$. It is designated by CAS Registry Number 84057-84-1 which is incorporated herein by reference. It can have the molecular structure:

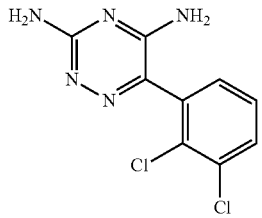 [SMILES: Nc1nnc(-c2cccc(Cl)c2Cl)c(N)n1]

LAMICTAL is commercially available in formulations for oral administration in 25 mg, 100 mg, 150 mg and 200 mg doses. In addition to lamotrigine, these table can also comprise any of the following components: lactose; magnesium stearate; microcrystalline cellulose; povidone; sodium starch glycolate; FD&C Yellow No. 6 Lake (100 mg tablet only); ferric oxide, yellow (150 mg tablet only); and FD&C Blue No. 2 Lake (200 mg tablet only), and combinations thereof.

LAMICTAL is also provided in the form of chewable dispersible tablets for oral administration. These tablets comprise 2 mg, 5 mg or 25 mg lamotrigine. In addition to lamotrigine, these tablets can also comprise any of the following components: blackcurrant flavor, calcium carbonate, low-substituted hydroxypropyl cellulose, magnesium aluminum silicate, magnesium stearate, povidone, saccharin sodium, and sodium starch glycolate, and combinations thereof.

LAMICTAL is also provided in the form of orally disintegrating tablets for oral administration. These tablets comprise 25 mg, 50 mg, 100 mg, or 200 mg lamotrigine. In addition to lamotrigine, these tablets can also comprise artificial any of the following components: cherry flavor, crospovidone, ethylcellulose, magnesium stearate, mannitol, polyethylene, and sucralose, and combinations thereof.

Bupropion

Bupropion (bupropion hydrochloride) is marketed under the tradenames WELLBUTRIN, ZYBAN, VOXRA, BUDEPRION, PREXATON, ELONTRIL and APLENZIN. It has also been referred to in the art as amfebutamone. Bupropion has the chemical structure (±)-1-(3chlorophenyl)-2-[(1,1-dimethylethyl)amino]-1-propanone hydrochloride. The molecular formula is $Cl_3H_{18}ClNO.HCl$. It is designated by CAS Registry Number CAS number 34841-39-9, which is incorporated herein by reference. It can have the molecular structure:

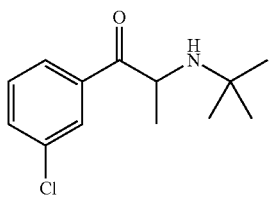 [SMILES: CC(NC(C)(C)C)C(=O)c1cccc(Cl)c1]

A Bupropion formula marketed under the tradename WELLBUTRIN is supplied for oral administration as 75-mg and 100-mg film-coated tablets. In addition to bupropion hydrochloride, each tablet can comprise any of the following components: 75-mg tablet—D&C Yellow No. 10 Lake, FD&C Yellow No. 6 Lake, hydroxypropyl cellulose, hypromellose, microcrystalline cellulose, polyethylene glycol, talc, and titanium dioxide; 100-mg tablet—FD&C Red No. 40 Lake, FD&C Yellow No. 6 Lake, hydroxypropyl cellulose, hypromellose, microcrystalline cellulose, polyethylene glycol, talc, and titanium dioxide, and combinations thereof.

A Bupropion formula marketed under the tradename WELLBUTRIN XL is supplied for oral administration as 150-mg and 300-mg extended-release tablets. In addition to bupropion hydrochloride, the tablets can comprise any of the following components: ethylcellulose aqueous dispersion, glyceryl behenate, methacrylic acid copolymer dispersion, polyvinyl alcohol, polyethylene glycol, povidone, silicon dioxide, and triethyl citrate, and combinations thereof.

The compositions of the invention can include lamotrigine, bupropion, pharmaceutically acceptable salts thereof, and combinations thereof. The compositions of the invention are pharmaceutical compositions that can be administered via any conventional route, including orally and intravenously. In certain embodiments, the compositions are administered orally. In certain embodiments, a first composition comprising lamotrigine can be administered. Optionally, a second, separate composition comprising bupropion can be administered. In certain embodiments, a first composition comprising bupropion can be administered, and a second, separate composition comprising lamotrigine can be administered. Dosing schedules and amounts of the active ingredients modified on a case-by case basis by one skilled in the art, given the benefit of the present invention. In general, dosing will be dependent on the age, gender, size, and overall health of the individual, whether or not any related neurological disorders are present, and the severity of the dizziness to be treated. In this regard, the amounts of lamotrigine for any particular patient can be tailored on a case by case basis in view of the present disclosure. The compositions of the invention can be formulated to provide controlled release of the ingredients, such that the ingredients can be released rapidly or slowly, as desirable.

The amount of lamotrigine dosage can be between 1.0 mg and 200.0 mg, inclusive, and inclusive of all integers there between to the first decimal point. In certain embodiments, the amount of lamotrigine in an individual dose is 2 mg, 5 mg, 25 mg, 100 mg, 150 mg or 200 mg. In certain embodiments, the dosage is 25 mg to 400 mg. The dosage can be adjusted as desired, such as by being increased in amounts of 25 mg at a time. The lamotrigine, whether administered alone or as part of combined treatment with Bupropion, can be administered, for example, once a day or twice a day.

In embodiments, the individual treated according to the present disclosure is administered a composition comprising lamotrigine at least once a day. In embodiments, the composition is administered more than once a day, such as at least twice a day. In embodiments, the composition is administered between once and twice a day, or is administered only once a day. In embodiment, lamotrigine is taken by the individual in an amount between 10 mg to 500 mg, inclusive, and including all integers and ranges of integers there between. In embodiments, between 25 mg to 200 mg of lamotrigine are administered twice daily (BID). In embodiments, the individual is treated for an initial period of time with a first dosage, and then is treated with a different dosage for a second period of time. In embodiments, the first period comprises a lower upper dosage than the second period. In one embodiment, the first period is considered a titration period and the second period is considered a maintenance period.

In one non-limiting embodiment, the individual is treated with between 25 mg to 200 mg BID for a period of between one and 4 weeks, inclusive and including all ranges of days there between. In embodiments, the first period dosage is between 25 and 50 mg BID lamotrigine. In embodiments, the individual is treated for the first period for a period of between two weeks and three months at the first dosage, and is treated during a second period for another at least one, two, three, or more months. The maintenance period can be extended indefinitely, and subsequent rounds of titration and maintenance can be used depending on a variety of factors, such as whether or not the individual discontinues the treatment, and whether or not the MD-associated vertigo returns. In embodiments, the maintenance period comprises treating the individual with from 25 mg BID and 200 mg BID, inclusive and including all integers and ranges there between. In embodiments, the maintenance dosage is 100 mg BID to 150 mg BID.

If Buproprion is also used, in certain embodiments, the amount of Bupropion in an individual dose can be between 50.0 mg and 450.0 mg, inclusive, and inclusive of all integers there between to the first decimal point. The dosage can be adjusted as desired, such as by being increased in amounts 75 mg to 450 mg. The dosage can be increased at, for example, increments of between 25 to 50 mg, and can be administered once or twice a day.

In certain embodiments, the invention is directed to prophylaxis and/or therapy of dizziness for any individual who has been diagnosed with or is at risk for dizziness, whether or not the individual presents with one or more neurological disorders correlated with the dizziness. In certain embodiments, the individual treated according to the method of the invention has not previously been diagnosed with, and/or has not been previously prescribed and/or treated with a composition of the invention for any one, or any combination of the following conditions: migraine headaches; depression; anxiety; smoking cessation; seizures or convulsions; epilepsy; bipolar disorder; peripheral neuropathy; trigeminal neuralgia; cluster headaches; neuropathic pain; a personality disorder; post-traumatic stress disorder; migraine-associated vertigo (MAV); phobic postural vertigo/chronic subjective dizziness (PPV/CSD); or selective serotonin reuptake inhibitor (SSRI)-induced sexual dysfunction. In embodiments, dizziness comprises vertigo.

Treatments according to the present invention can be carried out over various periods of time, during which the patients can be monitored for improvements in dizziness symptoms.

In another embodiment, the invention provides a method for diagnosing an individual as a candidate for dizziness/vertigo therapy. The method comprises testing an individual for dizziness and/or Meniere's Disease, and upon determining that the individual suffers from dizziness and/or Meniere's Disease, prescribing the individual therapy comprising administering to the individual a composition comprising Lamotrigine, Bupropion, or a combination thereof. In one embodiment, the method further comprises administering the composition to the individual.

It will be recognized from the foregoing that the present invention is based in part on our discovery that a commonly used anti-epileptic medication and combinations of it with other compounds may be effective to treat or prevent Meniere's attacks, and to alleviate dizziness associated with other conditions. Results reflecting this are presented in FIGS. 1-7 and support several aspects of approaching dizziness using single and combined pharmaceutical approaches.

Many patients complain of a very different dizziness or imbalance sensation in between Meniere's attacks. These symptoms usually last for a shorter period of time, from seconds to minutes; are positional movement related, like bending or turning too fast; and can be related to exposure to light, noise and crowded environments. Unlike the Meniere's attacks, the dizziness is not associated with severe vertigo, nausea and vomiting and the symptoms usually resolve in seconds or minutes. We believe this secondary dizziness is more likely diagnosed as phobic postural vertigo (PPV) or chronic subjective dizziness (CSD). We believe the composition sold under the trade name Wellbutrin XL is particularly well suited for the invention because it one of its major side effects is a reduced seizure threshold, which could be neutralized by combining it with Lamotrigine according to the invention, and thus, combination therapy using for Meniere's Patients using lamotrigen and buproprion is an aspect of this disclosure.

Without intending to be constrained by any particular theory, we believe that Meniere's attacks may be like "migraine in the inner ear" generated by unstable neuronal activity and this activity may be related to sodium channelopathy. So like anticonvulsants, Lamotrigine may either stop the generation of Meniere's attacks or prevent the propagation of Meniere's attacks from the ear to the central nervous system. Furthermore, Wellbutrin XL, as a norepinephrine reuptake inhibitor, may be raising dopamine levels in the brain and raising the threshold for neuronal activity, consequently preventing the generation of phobic postural vertigo or chronic subjective dizziness. Therefore, we believe that Lamotrigine may be able to stop the Meniere's attacks and Wellbutrin XL may be able to help the secondary phobic postural vertigo and underlying anxiety. Thus, in addition to the prophylactic and therapeutic approaches to treating dizziness, it is contemplated that the combination of Lamotrigine and Wellbutrin could be a effective treatment for Meniere's disease and may prevent permanent damage to the vestibular (imbalance and vertigo) and cochlear (hearing loss) functions, and also significantly improve the quality of the patient's life.

With respect to MAV, and again without wishing to be bound by any particular theory, we believe that a combination of Lamotrigine and Wellbutrin XL will send MAV disorders into remission. This is based on the idea that migraine-associated vertigo is a central phenomenon in which neuron activity is hyperactive and surpasses a dizziness threshold during the attacks. This neuron hyperactivity in the brain is similar to the activity seen in seizure patients and could be treated in a comparable manner. Anti-epileptics have successfully served as migraine prophylactic medications by mitigating neuron activity. However, FDA-approved Topiramate has several unwanted side effects, including confusion, slowed thinking, memory problems, trouble concentrating and kidney stones. Lamotrigine and Topiramate both act as anti-epileptic sodium channel blockers, but Lamotrigine has fewer risks and side effects. Accordingly, we propose that Lamotrigine will reduce the neuron activity and prevent the dizziness threshold from being reached without unwanted mental and physical reactions. Moreover, Wellbutrin XL will likely function as an effective supplemental anti-anxiety medication. Although tricyclic antidepressants were ranked low for relief of either migraine or vestibular symptoms, Wellbutrin XL is a nontricyclic antidepressant and still has the potential for relief.[xxiii] Evidence presented here as described further below shows that a pharmacotherapy comprising Lamotrigine and Wellbutrin XL could be an effective approach to treat the symptoms of a large population suffering from otherwise untreated dizziness problems. See FIGS. 1 and 2.

With respect to Phobic Postural Vertigo, both Meniere's disease and migraine-associated vertigo can have persisting dizziness even after the primary symptoms are treated. The residual imbalance can be from the vestibular disorder exacerbating previous anxiety conditions or from the new additional stress and anxiety of having the primary vestibular disorder. These psychological effects can be so great that they manifest into a secondary problem termed phobic postural vertigo (PPV). Holmber et al. describes PPV as "(i) dizziness and subjective disturbance of balance while standing or walking, despite normal clinical balance tests, (ii) fluctuating unsteadiness for seconds to minutes, or momentary perceptions of illusory body perturbations, (iii) usually a perceptual stimulus or social situation as a provoking factor with a tendency towards rapid conditioning, generalization and avoidance behavior, (iv) anxiety and vegetative symptoms during or after vertigo, (v) an obsessive-compulsive type personality, labile affect or mild depression and (vi) onset frequently after a period of emotional stress, a serious illness or a vestibular disorder".[xxiv] Although physical symptoms of the disorder fluctuate and can decrease in severity over time, complete recoveries are rarely made.[xxv] Research on cognitive behavioral therapy has shown only a limited long-term improvement for PPV patients, leaving many individuals to continue experiencing debilitating symptoms.[xxvi] The problem may not be in ineffective treatments, but in solutions that only address limited aspects of the disorder. Recently Staab et al. proposed the new term chronic subjective dizziness (CSD) to replace phobic postural vertigo. The primary criterion change lies in chronic subjective dizziness diagnoses requiring symptoms to exist for three months or more. More research on the treatment of PPV/CSD has been reported, mostly anti-anxiety medications[xxvii].

PPV is often observed in patients who are also diagnosed with migraine-associated vertigo; PPV has been observed in up to 30% of MAV patients during one study.[xxviii] Our own research has shown that PPV and MAV present non-statistically different clinical results during optokinetic (OPK) drum and rotary chair testing. Both groups of patients have dizziness complaints after OPK drum stimulation and showed either high gain or low gain patterns in the higher frequencies on the rotary chair testing.[xxix] This co-occurrence provides the possibility that these patients have both a lower dizziness threshold as well as the neuronal hyperactivity exhibited in phobic postural vertigo and migraine-associated vertigo patients, respectively. Therefore, the best management would include pharmaceutical treatment for both conditions, and for reasons stated above, the Lamotrigine-Wellbutrin XL combination would be a potential candidate for successful pharmacotherapy. Our research showed that antidepressants or anti-anxiety medications work well for patients with PPV/CSD. However, a combination of the Lamotrigine-Wellbutrin XL medications for this group of patients has had much more success. See FIGS. 3, 4, 5 and 6 and the description of results below.

It will be apparent to those skilled in the art from and the present description and Figures that the combination medication of Lamotrigine and Wellbutrin XL, as well as Lamotrigine alone, is likely able to raise dizziness thresholds and decrease the neuronal activity at the same time. Accordingly, we propose that the approaches disclosed herein should have greater efficacy for both types of dizziness/vertigo. Further, the combination of Lamotrigine and Wellbutrin may not only be effective for Meniere's disease, but also for patients with migraine-associated vertigo and phobic postural vertigo/chronic subjective dizziness. All three patient groups combined constitute almost two-thirds of the total dizziness population. Dizziness continues to be one of the most common clinical presentations; it is listed as the third most common reason for a doctor visit for those 60 years old or older and becomes the number one reason for a doctor visit for those over the age of 70. The neuronal "threshold" theory may be able to expand to other episodic neurologic or psychiatric disorders: like migraine, bipolar disorders, anxiety/panic or unexplained episodic neurologic spells. Neuronal hyperactivity happens in different parts of the brain and could then manifest as different symptoms. Therefore, we believe that the compositions and methods of the invention may be useful for a wide range of clinical applications for other episodic neurologic and psychiatric disorders in addition to the treatment of dizziness/vertigo.

EXAMPLE 1

This Example provides a description of experiments and results supporting the use of lamotrigine alone for prophylaxis and/or therapy if dizziness in MD patients.

Standard protocol approvals, registrations and patient consents. The State University of New York at Buffalo IRB approved this study.

Population. A retrospective and prospective review was performed on patients who were older than 18 years old, diagnosed with active definite MD at the Dent Dizziness, Balance and Tinnitus Center and treated with lamotrigine. Definite MD is defined as two or more episodes of vertigo that last for ≥20 minutes with documented hearing loss on at least one occasion, tinnitus and/or aural fullness, and other causes excluded. Active MD status requires patients to experience at least three vertigo attacks during the three months prior to treatment.

Clinical data. Data collected included demographic information, history of MD, prior medical treatment, clinical diagnosis, clinical presentation, stage of the disease, and frequency of Ménière's vertigo attacks prior to and after treatment. The staging of MD was based on the four-tone average of the pure-tone thresholds at 0.5, 1, 2 and 3 kHz of the worst audiogram during the six months before treatment. The questionnaires used were the Dizziness Handicap Inventory (DHI) and the Center's Dizziness Questionnaire. Current or past history of anxiety/depression, migraine problems, and use of anti-anxiety medication were also analyzed.

Outcome variable. The primary outcome measure was the reduction of Ménière's vertigo attacks at both three months after lamotrigine initiation (primarily the titration period) and three months after treatment at maintenance dosage. Secondary outcome measures included DHI scores and patient reports of clinical improvement. Data were confirmed by review of physicians' notes, vestibular and audiogram testing results, and supporting data. Means and standard deviations (SDs) were calculated for all continuous variables and proportions for all categorical variables. The primary research questions were whether or not lamotrigine led to a reduction of Meniere's vertigo attacks and whether or not lamotrigine led to improvement in quality of life for MD patients.

Statistical analysis. The overall difference in Meniere's vertigo attacks among 3 months pre-treatment, 3 months of titration, and 3 months of maintenance treatment was evaluated by Friedman's test, which is a nonparametric test for treatment differences in a randomized complete block design. The Wilcoxon signed rank sum test, which is the nonparametric version of a paired sample t-test, was used for the pairwise comparisons of Meniere's vertigo attacks from the three different time periods as well as DHI before and after treatment. Fisher's exact test was used to evaluate whether treatment effectiveness was affected by migraine or anxiety comorbidities. For all of these statistical tests, the tests were two-sided, and the level of significance was set to 0.05. Differences were considered significant if the p-value was less than 0.05.

The following results were obtained.

Clinical characteristics. 45 patients matched the criteria for the study, which are the following: diagnosis of active definite MD and prescription of lamotrigine. The mean age of the patient cohort was 61 years (SD 16.5). In terms of sex and race, 29 patients were female and 42 were Caucasian. There were 33 patients who had a history of anxiety/depression (73%), with 22 patients on anti-anxiety medication (49%), and 22 patients had a history of migraine (49%).

Based on the four-tone average, 7 patients were diagnosed with stage one (≤to 25 dB), 10 with stage two (between 26 and 40 dB), 19 with stage three (between 41 and 70 dB), and eight with stage four (>70 dB). There was one patient who did not have an audio report. The mean prior treatment DHI score was 47.6 (SD 19.6). The mean number of vertigo attacks during the three months prior to treatment was 12.7 (SD 11.6).

Lamotrigine titration. All 45 patients began a titration of lamotrigine of 25 mg BID for two weeks to 50 mg BID for two weeks. Final maintenance dosages varied between 25 mg BID and 200 mg BID due to individual patient tolerance and response; 29 patients were on either 100 mg BID or 150 mg BID maintenance dosages (64%). There was one patient who was lost to follow-up. There were four patients who discontinued lamotrigine due to side effects: one experienced stomachaches and diarrhea, one complained of hallucinations, and two developed rashes.

Figure 7:
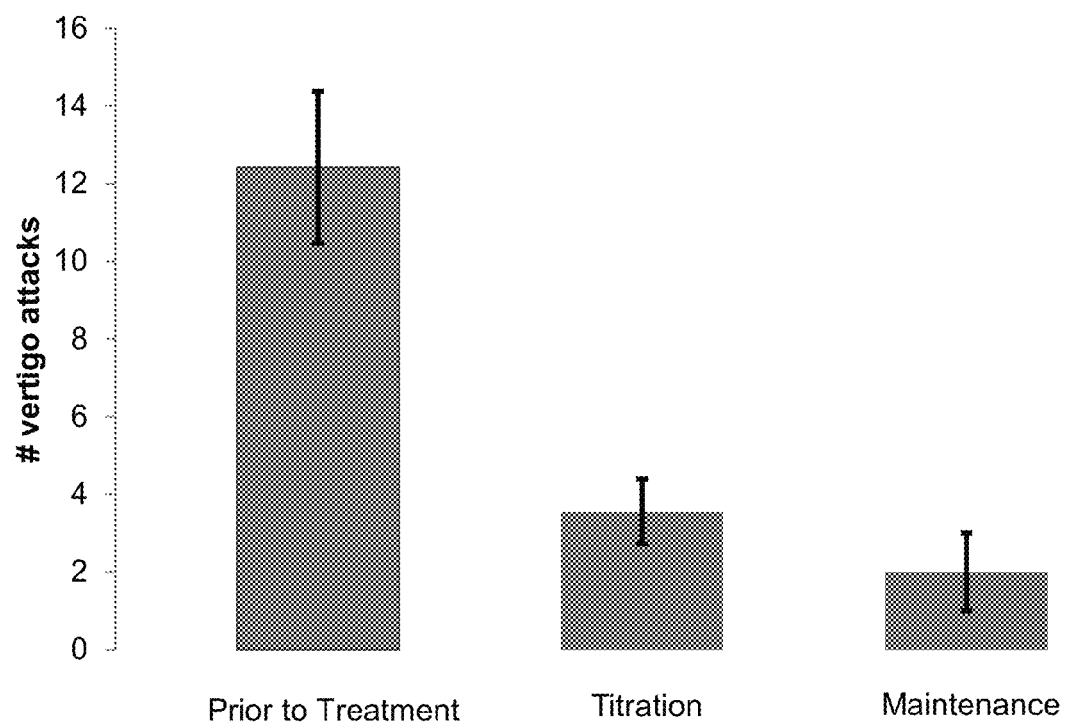
FIG. 7. Graph showing Improvement of Meniere's Vertigo Attacks with Lamotrigine Treatment. The data show there were significantly fewer vertigo attacks during the two lamotrigine treatment periods (3 months of titration period, 3 months of maintenance dosage) compared to the 3 months prior to treatment ($p<0.001$, $p<0.001$). There were also significantly fewer vertigo attacks during the 3 months after lamotrigine maintenance relative to the 3 months of titration ($p=0.04$).

Outcome after lamotrigine treatment. Out of all 45 study patients, 38 (84%) reported an improvement in Ménière's vertigo attacks with lamotrigine treatment. The mean number of vertigo attacks three months after initiation (primarily the titration period) was 4.5 (SD 6.2) and the mean number after three months of maintenance dosage was 1.9 (SD 4.6). There were significantly fewer vertigo attacks during these two treatment periods than the period prior to treatment (p<0.001, p<0.001; FIG. 7). There were also significantly fewer vertigo attacks during the 3 months of lamotrigine maintenance relative to the 3 months of titration (p=0.04; FIG. 7), indicating the dose effect of lamotrigine. More than half of the improved patients (21 of 38) had a complete resolution of their Ménière's vertigo attacks during the three month maintenance period. The mean post-treatment DHI score was 28.6 (SD 20.9). On average, the post-DHI score was 19 points less than the pre-DHI score; this difference was statistically significant (p=0.001).

Among the patients who reported improvement, there were 20 who had migraine and 28 with anxiety/depression disorder. However, vertigo attack reduction and remission were not affected by migraine (p=0.414) nor anxiety/depression (p=1.000) comorbidities (Table 1). These data reinforce the notion that lamotrigine was effective at treating Meniere's disease and not the comorbidities of the disease.

TABLE 1

Effectiveness of Lamotrigine for Meniere's vertigo attacks was not affected by the diagnosis of Migraine or Anxiety

|  | MD with migraine (anxiety) | MD without migraine (anxiety) | Total |
|---|---|---|---|
| Vertigo attack free | 11 (15) | 10 (6) | 21 |
| Vertigo reduced | 9 (13) | 8 (4) | 17 |
| Vertigo unchanged | 1 (1) | 1 (1) | 2 |
| Side effect | 1 (3) | 3 (1) | 4 |
| Lost to follow-up | 0 (1) | 1 (0) | 1 |

Vertigo attack reduction and remission were not affected by migraine (p=0.414) nor anxiety/depression (p=1.000) comorbidities.

While the invention has been described through specific embodiments, routine modifications will be apparent to those skilled in the art and such modifications are intended to be within the scope of the present invention.

[i] Baloh R W, Halmagyi G M, Zee D S. The history and future of neuro-otology. Continuum 2012; 18(5):1001-1015.

[ii] Lempert T. Recurrent Spontaneous Attacks of Dizziness. Continuum 2012; 18(5):1086-1101.

[iii] COMMITTEE ON HEARING AND EQUILIBRIUM, Members of the Committee on Hearing and Equilibrium: Edwin M. Monsell, MD, PhD, Chairman; Thomas A. Balkany, MD; George A. Gates, MD; Robert A. Goldenberg, MD; William L. Meyerhoff, MD, PhD; and John W. House, MD, Consultant., OTOLARYNGOL HEAD NECK SURG 1995; 113:181-5., Committee on Hearing and Equilibrium guidelines for the diagnosis and evaluation of therapy in Meniere's disease*, Otolaryngology—Head and Neck Surgery, Volume 113, Issue 3, September 1995, Pages 181-185, ISSN 0194-5998, 10.1016/S0194-5998(95)70102-8. (www.sciencedirect.com/science/article/pii/S0194599895701028)

[iv] Sajjadi H, Paparella M. Meniere's disease. Lancet 2008; 372:406-414.

[v] Lempert T. Recurrent spontaneous attacks of dizziness. Continuum 2012; 18(5):1086-1011.

[vi] Berlinger N T. Meniere's Disease: New concepts, new treatments. Minnesota Medicine November 2011; www-.minnesotamedicine.com/PastIssues/PastIssues2011/November2011/MenieresDisease.aspx

[vii] Radtke A, Lempert T, Gretsy M A, Brookes G B, Bronstein A M, Neuhauser H. Migraine and Meniere's disease: is there a link? Neurology 2002; 59:1700-1704.

[viii] Sajjadi H, Paparella M. Meniere's disease. Lancet 2008; 372:406-414; Strupp M, Thurtell M J, Shaikh A G, Brandt T, Zee D, Leigh J. Pharmacotherapy of vestibular and ocularmotor disorders including nystagmus. Neurology 2011; 258:1207-1222; Berlinger N T. Meniere's Disease: New concepts, new treatments. Minnesota Medicine 2011; November: www.minnesotamedicine.com/PastIssues/PastIssues2011/November2011/MenieresDisease-.aspx.

[ix] Baloh R W, Halmagyi G M, Zee D S. The history and future of neuro-otology. Continuum 2012; 18(5):1001-1015.

[x] Van Cruijsen N, Jaspers J P C, Van de Wiel H B M, Wite H P, Albers F W J. Psychological assessment of patients with Meniere's disease. International Journal of Audiology 2006; 45:496-502.

[xi] Kirby S E, Yardley L. The contribution of symptoms of posttraumatic stress disorder, health anxiety and intolerance of uncertainty to distress in Meniere's disease. J NervMent Dis 2009; 197:324-329.

[xii] McCall A A, Leary Swan E E, Borenstein J T, Sewell W F, Kujawa S G, McKenna M J. Drug delivery for treatment of inner ear disease: current state of knowledge. Ear & Hearing 2010; 31:156-65; Shea P F, Richey P A, Wan J Y, Stevens S R. Hearing results and quality of life after streptomycin/dexamethasone perfusion for Meniere's disease. The laryngoscope 2010; 122:204-211.

[xiii] Strupp M, Brandt T. Pharmacological advances in the treatment of neuro-otological and eye movement disorders. Current Opinion in Neurology 2006; 19:33-40.

[xiv] Gates G A. Meniere's Disease Review 2005. Journal of the AmericanAcademy of Audiology 2006; 17:16-26.

[xv] Lempert T. Recurrent Spontaneous Attacks of Dizziness. Continuum 2012; 18(5):1086-1101.

[xvi] Kayan A, Hood J D. Neuro-otological manifestations of migraine. Brain 1984; 107:1123-1142.

[xvii] Lempert T, Neuhauser H/Epidemiology of vertigo, migraine and vestibular migraine. Journal of Neurology 2009; 256(3):333-338.

[xviii] Neuhauser H, Leopold M, von Brevern M, Arnold G, Lempert T. The interrelations of migraine, vertigo, and migrainous vertigo. Neurology 2001; 56(4):436-441.

[xix] Cha Y, Baloh R. Migraine associated vertigo. Journal of Clinical Neurology 2007; 3:121-126.

[xx] Furman J, Marcus D. Migraine and motion sensitivity. Continuum 2012; 18(5):1102-1117.

[xxi] Breslau N, Schultz L R, Stewart W F, et al. Headache types and panic disorder: directionality and specificity. Neurology 2001; 56(3):350-354.

[xxii] Eckhardt-Henn A, Best C, Bense S, Breuer P, Diener G, Tschan R, et al. Psychiatric comorbidity in different organic vertigo syndroms. Journal of Neurology 2008; 255:420-28.

[xxiii] Bikhazi P, Jackson C, Ruckenstein M J. Efficacy of antimigrainous therapy in the treatment of migraine-associated dizziness. American Journal of Otolaryncology 1997; 18(3):350-354.

[xxiv] Holmber J, Karlber M, Harlacher U, Magnusson M. Experience of handicap and anxiety in phobic postural vertigo. ActaOto-Laryngologica 2005; 125:270-275.

[xxv] Huppert D, Strupp M, Rettinger N, et al. Phobic postural vertigo—a long-term follow up (5-15 years) of 106 patients. Journal of Neurology 2005; 252(5):564-569.

[xxvi] Holmber J, Karlberg M, Harlacher U, Magnusson M. One-year follow-up of cognitive behavioral therapy for phobic postural vertigo. Journal of Neurology 2007; 254: 1189-1192.

[xxvii] Staab J, Ruckenstein M, Amsterdam J. A prospective trial of sertraline for chronic subjective dizziness. The Laryngoscope 2004; 114: 1637-1641; Horii A, Uno A, Kitahara T, Mitani K, Masumura C, Kizawa K, Kubo T. Effects of fluvoxamine on anxiety, depression, and subjective handicaps of chronic dizziness patients with or without neuro-otologic diseases. Journal of Vestibular Research 2007; 17:1-8; Staab J, Ruckenstein J. Chronic dizziness and anxiety: Effect of course of illness on treatment outcome. Archives of Otolaryngology-Head & Neck Surgery 2005; 131(8):675-679.

[xxviii] Eggers S D, Staab J P, Neff B A, et al. Investigation of the coherence of definite and probable vestibular migraine as distinct clinical entities. Otology & Neurotology 2011; 32(7):1144-1151.

I claim:

1. A method for therapy of dizziness in an individual diagnosed with Meniere's Disease comprising administering to the individual a pharmaceutical composition comprising an effective amount of lamotrigine or a pharmaceutically acceptable salt thereof such that dizziness in the individual is lessened subsequent to the administration, wherein the lamotrigine or the pharmaceutically acceptable salt thereof is the only bioactive compound in the pharmaceutical composition, and wherein the effective amount of lamotrigine comprises between 25 mg and 200 mg of the lamotrigine administered twice daily.

2. The method of claim 1, wherein the twice daily administration is performed for a period of at least two weeks.

3. The method of claim 1, wherein the twice daily administration is performed for a period of at least three months, and wherein the individual experienced at least ten episodes of Meniere's Disease dizziness prior to being administered a first dose of lamotrigine or a pharmaceutically acceptable salt thereof, and wherein during the period of at least three months of the twice daily administration the individual experiences no more than 5 episodes of Meniere's Disease dizziness.

* * * * *